(12) United States Patent
Fujii (10) Patent No.: US 10,786,405 B2
(45) Date of Patent: Sep. 29, 2020

(54) WATERPROOF EXTERNAL INJURY PROTECTOR

(71) Applicant: Try and E Co., Ltd., Kobe-Shi, Hyogo (JP)

(72) Inventor: Takahiro Fujii, Kobe (JP)

(73) Assignee: Try and E Co., Ltd., Kobe-Shi (JP)

( * ) Notice: Subject to any disclaimer, the term of this patent is extended or adjusted under 35 U.S.C. 154(b) by 283 days.

(21) Appl. No.: 15/738,582

(22) PCT Filed: Jun. 6, 2016

(86) PCT No.: PCT/JP2016/066722
§ 371 (c)(1),
(2) Date: Dec. 21, 2017

(87) PCT Pub. No.: WO2017/212517
PCT Pub. Date: Dec. 14, 2017

(65) Prior Publication Data
US 2018/0168895 A1 Jun. 21, 2018

(51) Int. Cl.
*A61F 5/00* (2006.01)
*A61F 15/00* (2006.01)
(Continued)

(52) U.S. Cl.
CPC ............ *A61F 15/004* (2013.01); *A61F 13/00* (2013.01); *A61F 13/041* (2013.01); *A61F 13/043* (2013.01)

(58) Field of Classification Search
CPC ....... A61F 15/004; A61F 13/00; A61F 13/041
(Continued)

(56) References Cited

U.S. PATENT DOCUMENTS

| 4,639,945 A * | 2/1987 | Betz ................. A61F 15/00 2/22 |
| 5,016,648 A * | 5/1991 | Brown ............. A61F 13/041 128/846 |

(Continued)

FOREIGN PATENT DOCUMENTS

| CN | 102396804 A | 4/2012 |
| JP | S49-019969 A | 2/1974 |

(Continued)

*Primary Examiner* — Anna K Kinsaul
*Assistant Examiner* — Camtu T Nguyen
(74) *Attorney, Agent, or Firm* — James Judge (57) ABSTRACT

External-injury waterproof protector, of long service life as a product. The structure of the limb-insertion opening enables completely shielding out water to protect an injured area. The protector has a flexible pouch body composed of a waterproofing material, with a mouth at either one or both ends, and an extensible/contractible annular constriction component hermetically and adhesively attached to the one or both pouch-body end(s). The annular constriction component is furnished with a tube portion formed to enable covering a portion of the four human limbs in a watertight state, and a brim portion formed projecting radially outward from a mouth edge of the tube portion. The tube portion favorably is formed at a narrower diameter than that of the other end of the pouch body. The brim portion arcuately slopes gently in a flaring form, lending the mouth of the annular constriction component an arcuate sloping surface.

12 Claims, 7 Drawing Sheets

(51) Int. Cl.
*A61F 13/00* (2006.01)
*A61F 13/04* (2006.01)

(58) Field of Classification Search
USPC .............................................................. 602/3
See application file for complete search history.

(56) References Cited

U.S. PATENT DOCUMENTS

| | | | |
|---|---|---|---|
| 5,728,052 A * | 3/1998 | Meehan | A61F 13/041 |
| | | | 602/3 |
| 6,210,352 B1 * | 4/2001 | Williams | A61F 15/004 |
| | | | 128/849 |
| 6,895,971 B1 | 5/2005 | Evans | |
| 8,056,148 B1 | 11/2011 | Ballantyne et al. | |
| 2010/0249681 A1 * | 9/2010 | Brown | A61F 13/041 |
| | | | 602/3 |

FOREIGN PATENT DOCUMENTS

| | | |
|---|---|---|
| JP | S54-069027 U | 5/1979 |
| JP | S55-25094 U | 2/1980 |
| JP | S62-056023 U | 4/1987 |
| JP | 2003-201608 A | 7/2003 |
| JP | 2004-156155 A | 6/2004 |
| JP | 2004-215754 A | 8/2004 |
| JP | 2005-009035 A | 1/2005 |
| JP | 2008-169503 A | 7/2008 |
| JP | 4109996 B2 | 7/2008 |
| JP | 4818129 B2 | 11/2011 |
| WO | WO-2016-019928 A1 | 2/2016 |

* cited by examiner

WATERPROOF EXTERNAL INJURY PROTECTOR

TECHNICAL FIELD

The present invention relates to waterproof protectors, and principally to the waterproofing structure of waterproof protectors for external injuries.

BACKGROUND ART

To date, in cases where an arm or a leg is fractured and a cast is fitted on, or where an injury is sustained, it is necessary to keep the affected area of the limbs, or the cast on the fracture from getting wet in water. As a simple measure in showering or bathing, and in cooking, etc., the cast or the location of the limb injury is wrapped in a plastic bag or the like, and the water-intrusion mouth is bound with string or a rubber band. Nevertheless, cases where only one arm can be used have to be dealt with by someone else lending a hand, and completely sealing shut the water-intrusion mouth proves to be challenging.

In order to resolve these problems, a variety of waterproofing outfits have been marketed. For example, there is a product called Dry Socks™ made of a highly elastic material such as latex-rubber to fit the form of the four limbs. Designed for waterproofing effectiveness, the socks have an opening of diameter smaller than the body's limbs, and by inserting the injured arm or leg in a cover and immobilizing it, and with a rubber bulb purging air from an air-purge hole provided in the exterior side of the cover to make it airtight, the cover is adhered tightly to the arm or leg by the hermetic sealing. Whereas put into a vacuum state by purging air from the air hole, the air-purging waterproof covers show waterproofing effectiveness, nevertheless, discomfort occurs in the injured areas when put into a vacuum state, and moreover, the covers are inappropriate for casts on fractured bones, and with the diameter of the cover entrance being small, inserting the plaster part is challenging. And as precedent technology, the inventive concept involving Patent Document 1, likewise as with the above-discussed product, proposes a waterproofing garment with an attached exhaust tube, yet the problems of the time and effort to purge air, and the discomfort in wearing the garment, remain.

Further, as a simplified waterproofing cover, there is a product, produced from polyvinyl chloride, made to fit the shape of the body's limbs, and on the inner side of an opening in the cover it is furnished with a circular frame, and with an elastic clasp and a fastening mouth, wherein the injured region is inserted and immobilized. In this instance, the fastening mouth fulfills the role of waterproofing. With this waterproofing cover, the elastic fastening mouth is exploited to have the cover function to immobilize and waterproof the injured area, yet there is still a danger of the waterproofing ability being insufficient such that water will invade. Furthermore, the circular frame, being hard, imparts extraordinary discomfort and gives rise to strange sensations when the waterproofing cover is in operation, and, not keeping up its end of the bargain, the frame is prone to reverting, such that the cover fails to demonstrate complete waterproofing effectiveness. With the prior art as well, although the invention in Patent Document 2 proposes a waterproofing protector with an opening larger than the four limbs, and in which the opening is sealed off with a circular clasping belt, here too, the problem of having to get someone else to lend a hand to deal with cases where only one arm can be used remains.

Various inventions have been proposed as improvements of the above-discussed products and invention. The innovation involving Patent Document 3 is characterized in being configured with a tubular, rubber cover body that is opened on either end, annular constricting portions formed on the openings, and a moisture-absorbing element arranged along the inner periphery of the rubber cover body. Also, the invention involving Patent Document 4 is a protecting implement containing a flexible sleeve of a waterproofing material closed at one end and opened at the other, with a pliant and extensible/contractible rubber spacer membrane hermetically and adhesively attached to the other end, wherein with the sleeve pulled taught, the stretched opening prevents water from invading onto a cast or bandages, etc. Not unsurprisingly, with these implements there are no strange sensations, and the wearable articles can be put on single-handedly.

Patent Document 2: Japanese Unexamined Pat. App. Pub. No. 2005-66301.

Patent Document 3: Japanese Utility Model Registration No. 3038365.

Patent Document 3: U.S. Pat. No. 7,955,284

SUMMARY OF INVENTION

Issues Invention is to Address

Figure 7A:
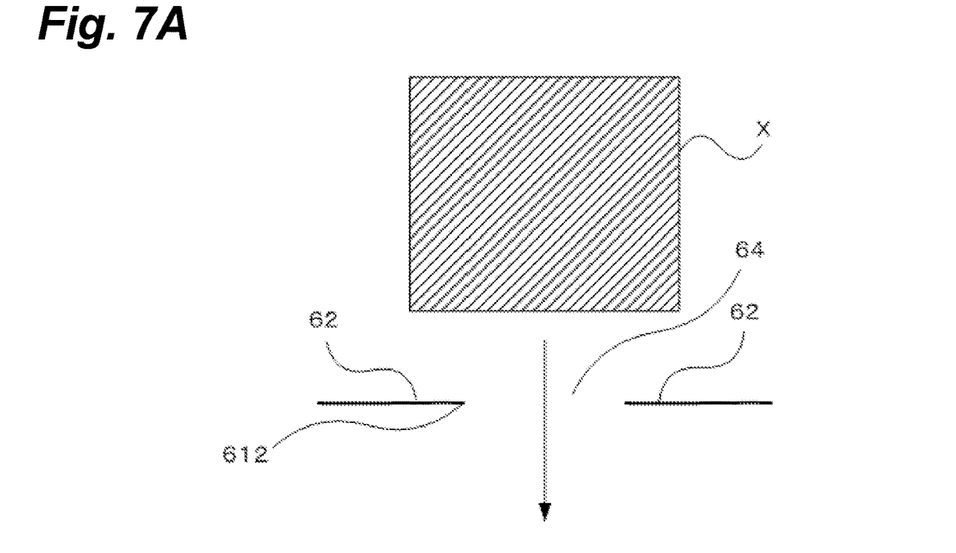
FIG. 7 is diagrams representing situations of change in putting an insertion object into, and taking it out of, the mouth of one example of a conventional product.
Figure 7B:
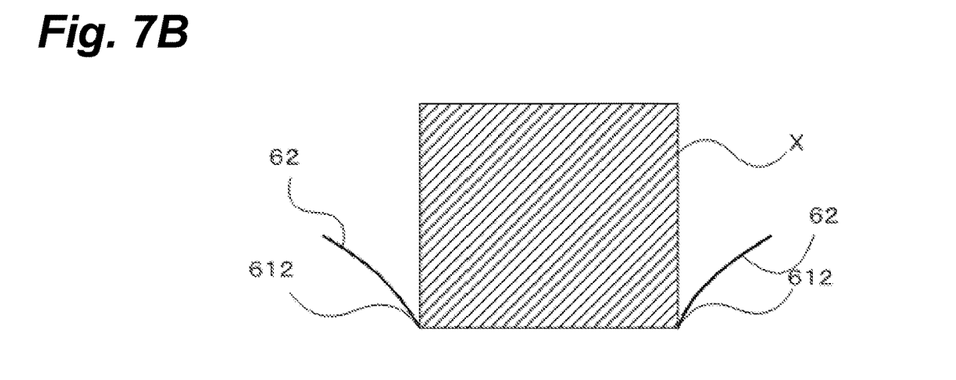
Figure 7C:
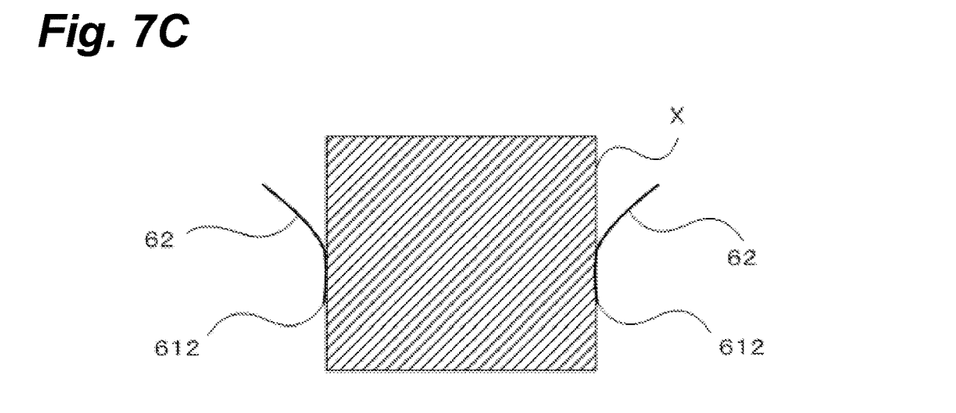

Nevertheless, with regard to the inventions and innovations involving Patent Documents 3 and 4, putting into and taking out of the arm/leg insertion opening an arm or leg that is larger than the mouth causes splitting, tearing, or fraying along the rim of the opening, which risks inviting the invasion of water. Reference is made to FIG. 7. FIG. 7 is diagrams representing an example of a conventional product, wherein the state of the opening rim-edge portion when an arm or leg is being put into or taken out of the opening is illustrated in particular. A more detailed description will be made. Referring to FIGS. 7A, 7B and 7C, a situation where an insertion object X of rectangular cross-section larger than the diameter of the mouth is being inserted through the mouth may be understood. Namely, when the insertion object X is inserted into the mouth 64, the rim edge 612 of the membrane constituting the mouth abuts against the insertion object X, widening out the mouth 64. This then means that also when the insertion object X is discharged from the mouth 64, the discharge takes place with the insertion object X being in abutment against the rim edge 612 immediately prior to being discharged. Thus, the edge rim 612 becomes abraded on occasions when the insertion object X is put into our taken out of the mouth 64, with the splitting, tearing, or fraying along its rim edge risking that invasion of water is incurred. Therein, an object of the present invention, taking into consideration the above-described circumstances, is to make available a waterproof protector for external injuries, of long lifespan as a product, that by improving the opening structure through which an arm or leg is inserted enables completely shielding out water to protect an injured area.

Ways of Addressing the Issues

In order to accomplish the just-stated objective, an external-injury waterproof protector involving the present invention is a waterproof protector furnished with: a flexible pouch body composed of a waterproofing material and having a mouth at either one end or both ends; and an extensible/contractible annular constriction component hermetically and adhesively attached to either the one end or to both ends of the pouch body; characterized in that the annular constriction component is furnished with a tube portion formed so as to enable covering a portion of the four human limbs in a watertight state, and a brim portion formed projecting radially outward from a mouth edge of the tube portion. Here, the tube portion may be formed at a narrower diameter than that of the other end of the pouch body. Also, by making the brim portion arcuately slope gently in a flaring form so that the mouth of the annular constriction component is furnished with an arcuate sloping surface, the strength of the opening is increased.

Further, constituting the annular constriction component from silicone rubber is optimal. Meanwhile, the pouch body may be made composed from polyvinyl chloride, polyurethane, or α olefins. The pouch body and the annular constriction component may then be welded to each other by heat sealing, or may be bonded using a cement having a cyanoacrylate as its principal component.

Effects of Invention

According to an external-injury waterproof protector involving the present invention, the complete shielding out of water to protect an injured area is made possible, and the increasing of the strength of the opening is effective to enable withstanding long-term use.

MODES FOR EMBODYING INVENTION

Hereinafter, based on the drawings, an explanation of modes of embodying the present invention will be made in detail. In the drawings, with identical parts being labeled with identical reference numbers, reduplicating explanations will be omitted. Also, it should be borne in mind that in some cases the drawings represent exaggeratedly for the sake of understanding the present invention, and they have not necessarily been rendered to scale nor in minute detail. And it will be appreciated that the present invention is not limited to the embodying modes set forth in the following.

First Embodiment Example

Embodiment Example 1 will be described in detail with reference to the drawings.

Figure 1:
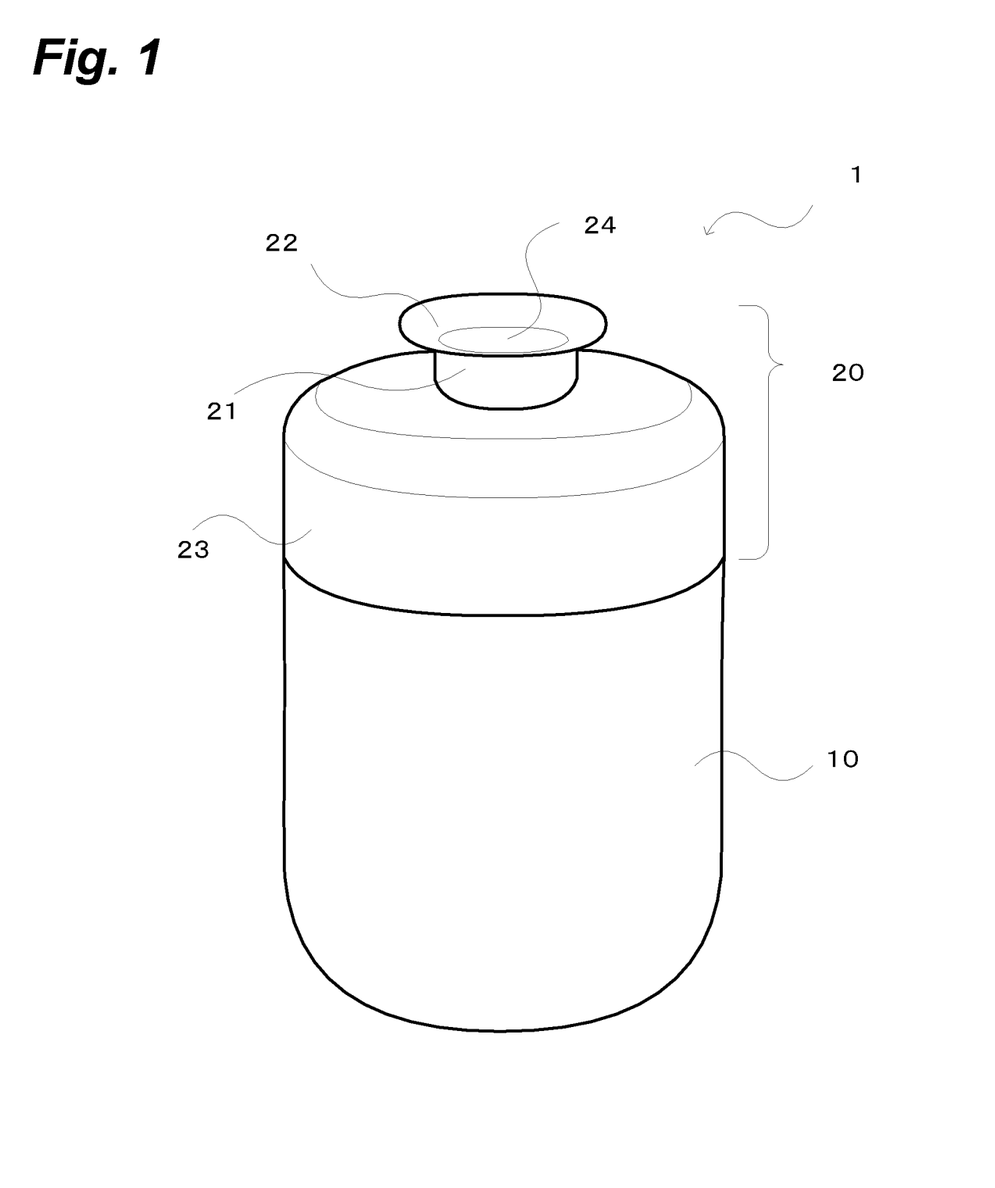
FIG. 1 is an oblique view schematically illustrating an external-injury waterproof protector of the present invention.

FIG. 1 is an oblique view schematically illustrating an external-injury waterproof protector in Embodiment 1 of the present invention.

Reference is made to FIG. 1. An external-injury waterproof protector 1 is furnished with a flexible pouch body 10 composed of a waterproofing material and having a mouth at one end and whose other end is closed, and an extensible/contractible annular constriction component 20 hermetically and adhesively attached to the one end of the pouch body 10.

The annular constriction component 20 is furnished with a tube portion 21 formed so as to enable covering a portion of the four human limbs (arms, legs) in a watertight state, and a brim portion 22 formed projecting radially outward from a mouth edge of the tube portion 21, with a mouth 24 being furnished in the middle of the brim portion 22. Further, the annular constriction component 20 is furnished with a joining portion 23 that attaches to the mouth of the pouch 10. Advantageously the mouth 24 of the annular constriction component 20 is furnished with an arcuate sloping surface 212 by the brim portion 22 arcuately sloping gently in a flaring form. Further, the tube portion 21 favorably is formed at a narrower diameter than that of the mouth of the pouch body 10. It is to be noted that the material for the annular constriction component 20 is not particularly restricted as long as it is pliant and extensible/contractible; the component 20 is advantageously made of silicone rubber.

The pouch 10 is favorably made in various lengths adapted to hand-/arm-use and foot-/leg-use applications as well as to adult-use, child-use and similar attributes, utilizing polyvinyl chloride, polyurethane, or α olefins as the material. Here, the pouch 10 and the annular constriction component 20 may be welded to each other by means of heat-sealing, or may be bonded by means of an adhesive whose principal component is a cyanoacrylate.

Reference is made to FIGS. 2 and 3. FIG. 2 is elevational views illustrating situations where the mouth 24 of the annular constriction component 20 is being extended/constricted. FIG. 3 is configurational outline diagrams schematically illustrating situations of change in the arcuate sloping surface 212, formed along the brim portion 22 and the tube portion 21, when widening out the mouth 24 of the annular constriction component 20.

Figure 2A:
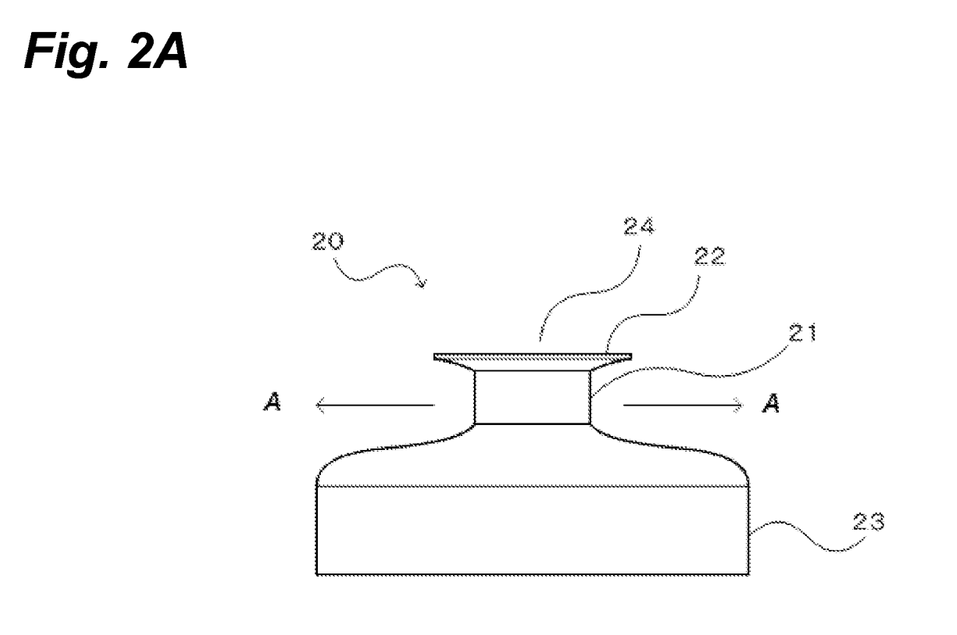
FIG. 2 is elevational views illustrating situations where the mouth of the annular constriction component is being extended/constricted.
Figure 2B:
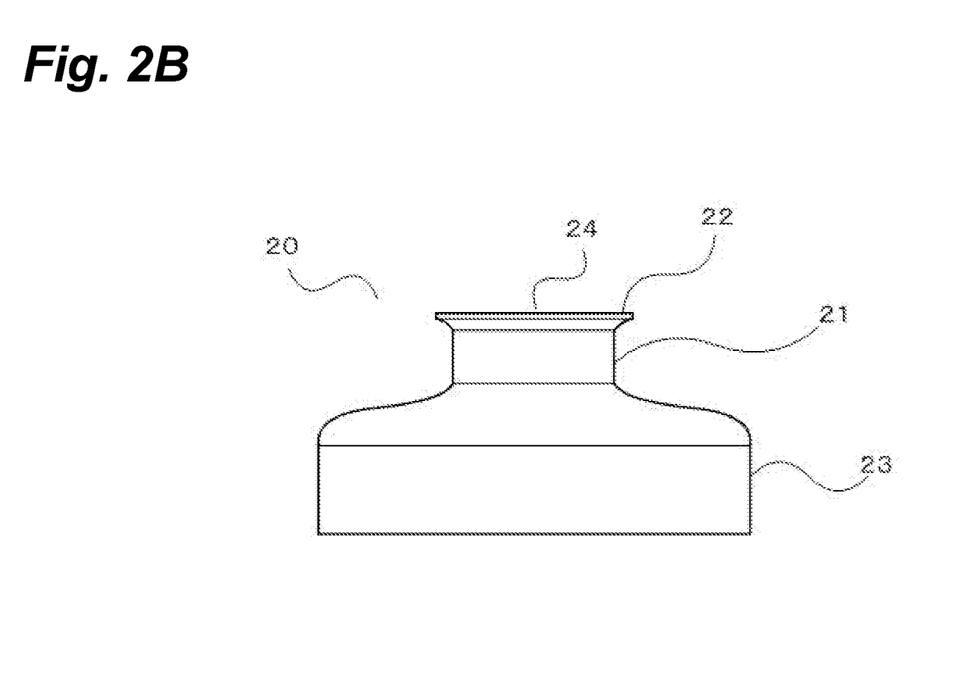
Figure 3A:
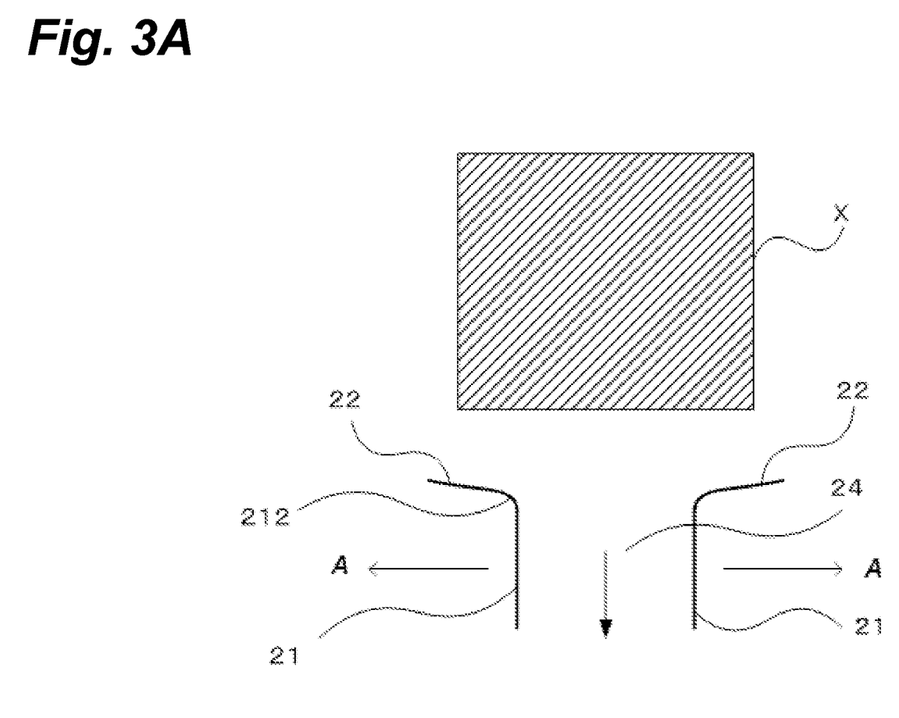
FIG. 3 is configurational outline diagrams schematically illustrating situations of change in the entry/exit receiving surface, formed along the brim portion and the tube portion, when widening out on the mouth of the annular constriction component.
Figure 3B:
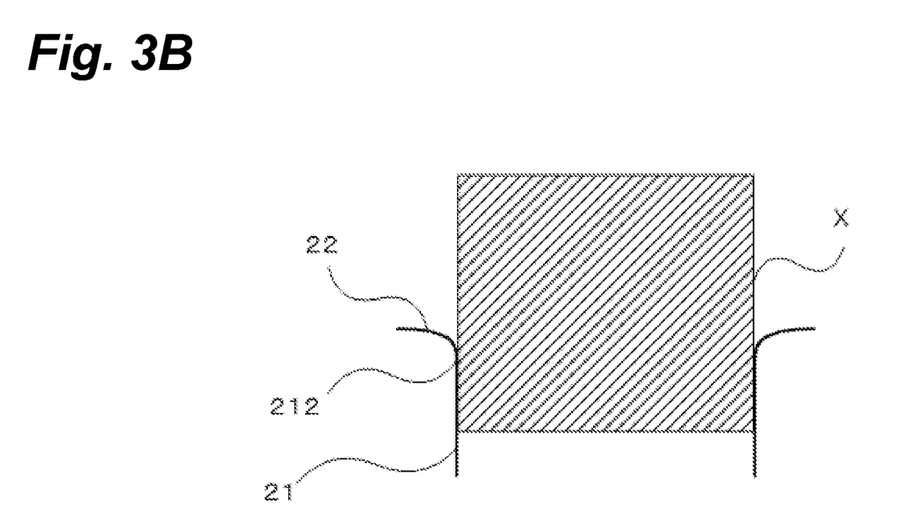

Reference is made to FIG. 2. Inserting an arm or a leg through the mouth of the annular constriction component 20 widens out the tube portion 21, represented basically in FIG. 2A, circumferentially (way of the arrows A), and the tube portion 21 expands as indicated in FIG. 2B. Rendering this schematically is as illustrated in FIG. 3. FIG. 3 will be explained in detail. Here, it should be borne in mind that while what is put into and taken out of the mouth 24 is an arm or a leg, in FIG. 3, the illustrating is done utilizing an insertion objection X that is rectangular in cross-section in order to make a contrastive comparison with FIG. 7. Referring to FIGS. 3A and 3B, a situation where the insertion object X, of rectangular cross-section that is larger than the diameter of the mouth 24, is being inserted through the mouth 24 may be understood. Namely, when the insertion object X is inserted into the mouth 24, the insertion object X abuts against the arcuate sloping surface 212 that constitutes the mouth, widening out the mouth 24. This then means that also when the insertion object X is discharged from the mouth 24, the discharge takes place with the insertion object X being in abutment against the arcuate sloping surface 212 immediately prior to being discharged. Thus, whereas the mouth edge rim 612 in the conventional product of FIG. 7 grows abraded on occasions when the insertion object X is put in our taken out, in the waterproof protector 1 involving the present invention, what is abutted against in an insertion object being taken out and put in is not the edge of a membrane constituting the mouth, but the arcuate sloping surface 212 that is constituted at the border between the tube portion 21 and the brim portion 22, such that a surface, not a line, receives the insertion object, making it possible to prevent splitting, tearing, or fraying along the peripheral end of the mouth 24, and to prolong the lifespan of the protector as well.

Figure 4:
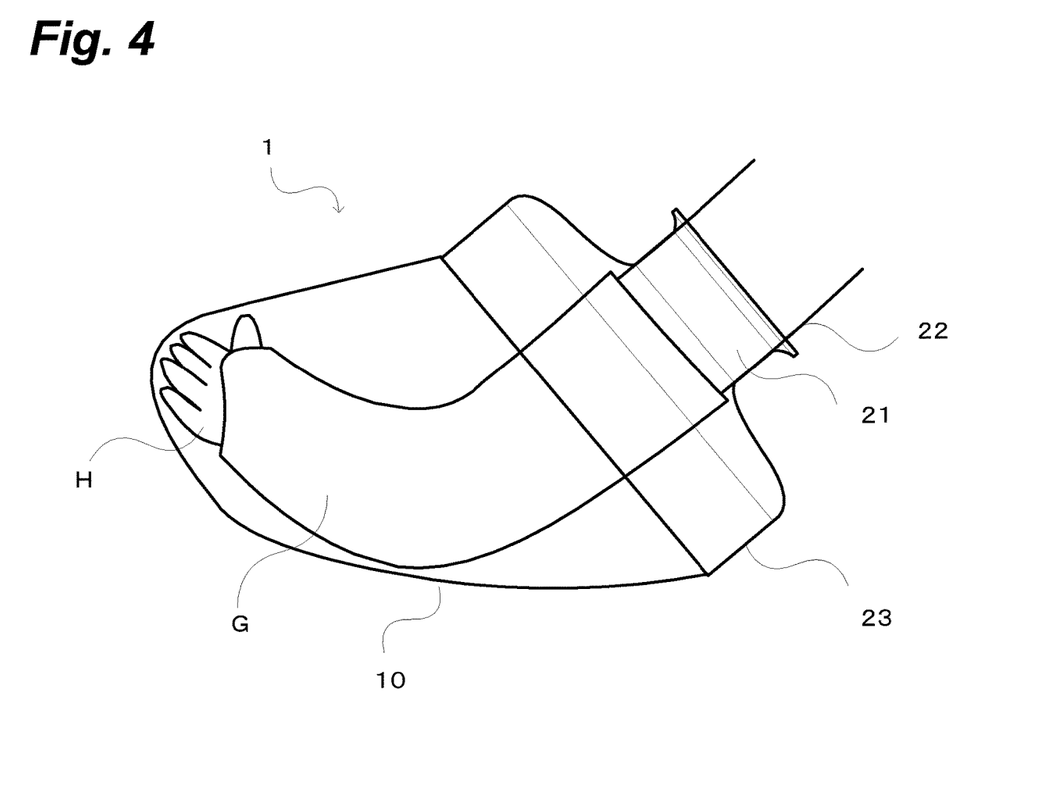
FIG. 4 is a diagram illustrating a state in which a waterproof protector of the present invention has been fitted onto an arm.
Figure 5:
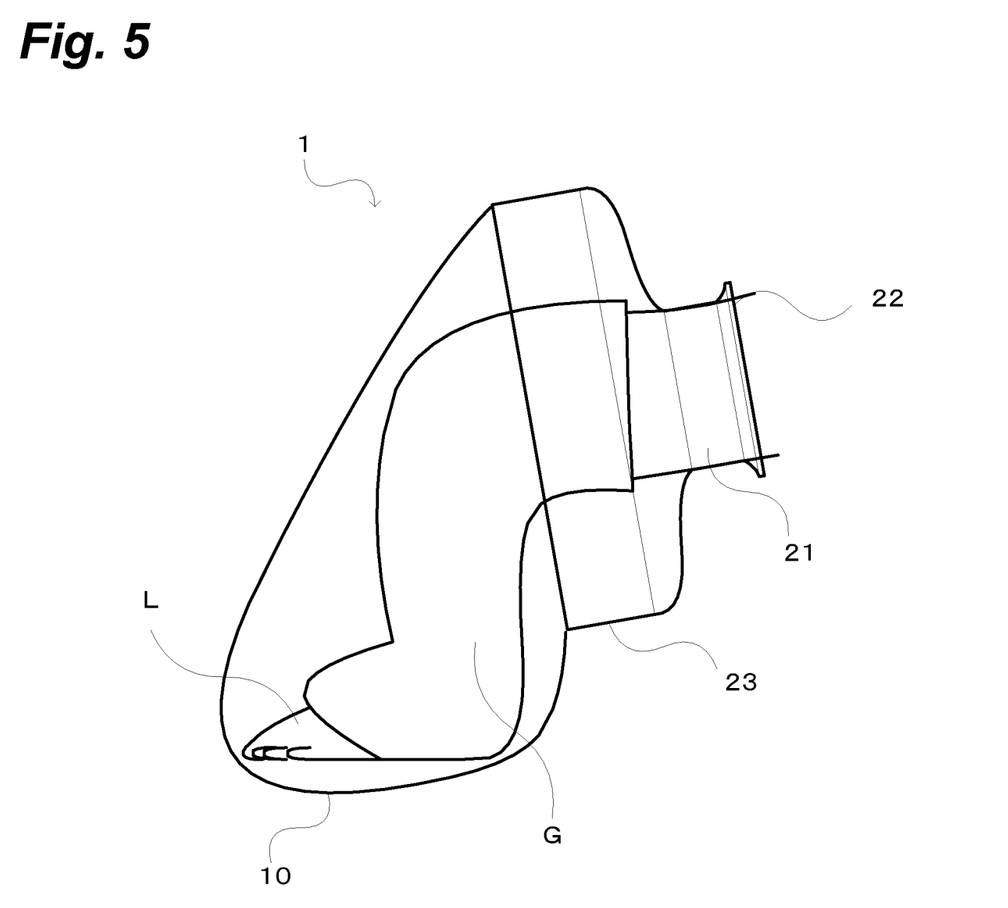
FIG. 5 is a diagram illustrating a state in which a waterproof protector of the present invention has been fitted onto a leg.

FIGS. 4 and 5 illustrate use examples. FIG. 4 illustrates a state in which a waterproof protector 1 of the present invention has been fitted onto an arm, and FIG. 5 illustrates a state in which a waterproof protector 1 of the present invention has been fitted onto a leg. It will be appreciated that forming the mouth 24 of size suited to the wrist or ankle, and forming the pouch 10 of size suited to the length of the arm or leg, are favorable.

Second Embodiment Example

Embodiment Example 2 will be described in detail with reference to the drawings.

Figure 6:
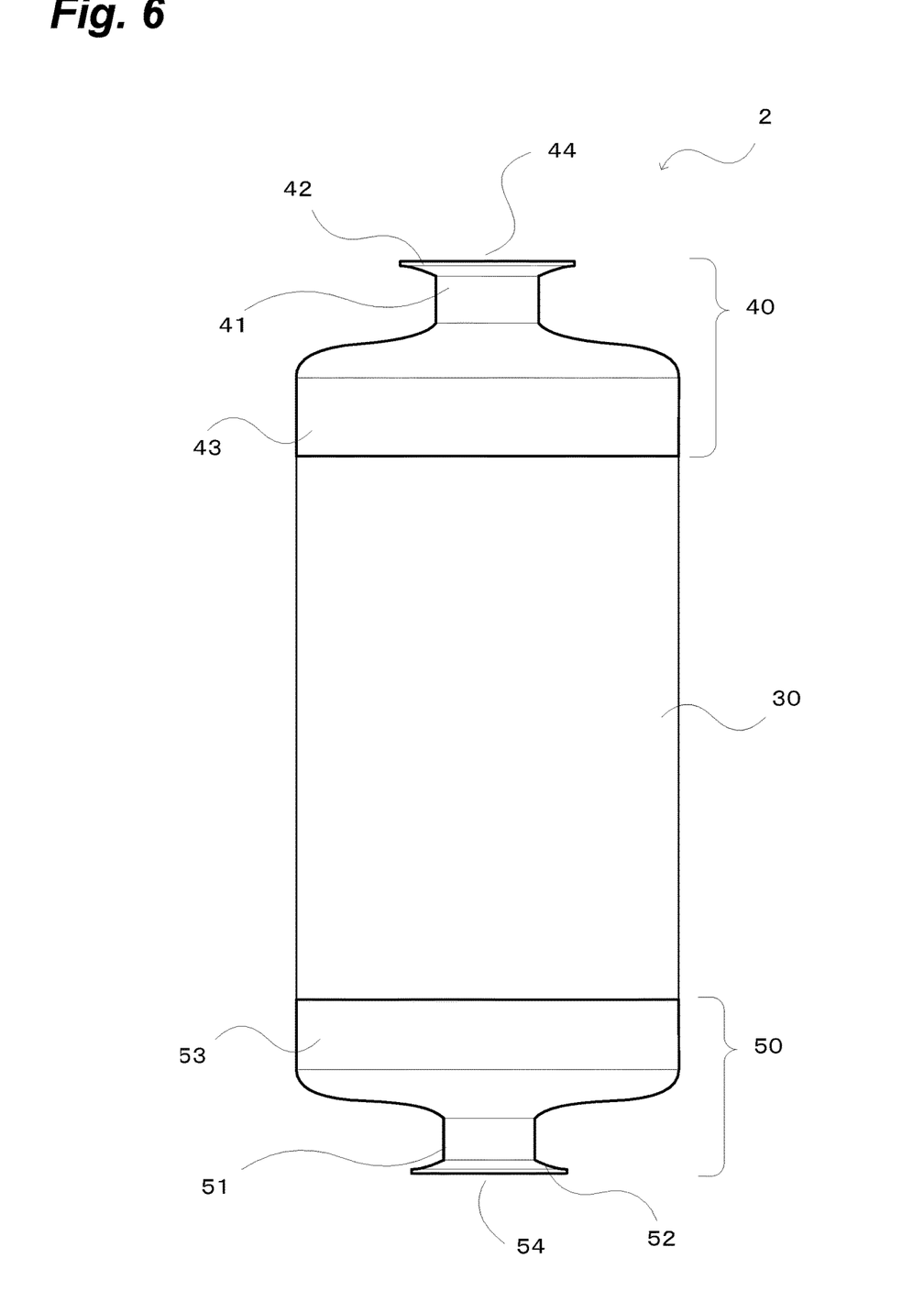
FIG. 6 is an elevational view schematically illustrating an external-injury waterproof protector 2 of the present invention.

FIG. 6 is an elevational view schematically illustrating an external-injury waterproof protector 2 of Embodiment Example 2 of the present invention.

Reference is made to FIG. 6. The external-injury waterproof protector 2 is furnished with: a flexible pouch body 30, having openings at either end, composed of a waterproofing material; and extensible/contractible annular constriction components 40 and 50, hermetically and adhesively attached to both ends of the pouch body 30.

The annular constriction component 40 is furnished with a tube portion 41 formed so as to enable covering a portion of the four human limbs (arms, legs) in a watertight state, and a brim portion 42 formed projecting radially outward from a mouth edge of the tube portion 41, with a mouth 44 being furnished in the middle of the brim portion 42. Further, the annular constriction component 40 is furnished with a joining portion 43 that attaches to the mouth of the pouch 30. By making the brim portion 42 arcuately slope gently in a flaring form so that the mouth 44 of the annular constriction component 40 is furnished with an arcuate sloping surface 412 (not illustrated), the strength of the mouth rim is increased. The tube portion 41 favorably is formed at a narrower diameter than that of the mouth rim of the pouch body 30.

The annular constriction component 50, likewise as with the annular constriction component 40, is furnished with a tube portion 51, and a brim portion 52 formed projecting radially outward from a mouth edge of the tube portion 51, with a mouth 54 being furnished in the middle of the brim portion 52. Further, the annular constriction component 50 is furnished with a joining portion 53 that attaches to the mouth of the pouch 30. By making the brim portion 52 arcuately slope gently in a flaring form so that the mouth 54 of the annular constriction component 50 is furnished with an arcuate sloping surface 512 (not illustrated), the strength of the mouth rim is increased. Further, the annular constriction component 50 is furnished with a joining portion 53 that attaches to the mouth of the pouch 30. The tube portion 51 favorably is formed at a narrower diameter than that of the mouth of the pouch body 30.

Since it has the annular constriction components 40 and 50, the external-injury waterproof protector 2 can be exploited in situations where there is an external injury to the midportion of an arm or leg, and it is desired to expose the tip of the hand or the tip of the foot. Accordingly, one of either of the tube portions 41 and 51 of the annular constriction components 40 and 50 is advantageously made narrower-diameter than the other.

The point of distinction between the external-injury waterproof protector 2 and the external-injury waterproof protector 1 is in the difference of whether there is an annular constriction component on a single end or on both ends; explanation of other points, being for the most part the same, is omitted.

In the foregoing, preferred embodiments in configurational examples of external-injury waterproof protectors of the present invention have been described, but it will be appreciated that various modifications are possible without departing from the technical scope of the present invention.

INDUSTRIAL UTILIZABILITY

Since external-injury waterproof protectors of the present invention may be utilized when it is desired not to let get wet with water limbs that are in a plaster cast or in a synthetic cast, artificial legs, limbs in splints or bandages, and limbs with burns, rashes, lacerations, athlete's foot, atopic dermatitis etc., they find wide utilization not only in household uses, but also as wearable articles for bathing in hospitals and nursing care facilities, etc.

LEGEND 1, 2: external-injury waterproof protector
10, 30: pouch body
20, 40, 50: annular constriction component
21, 41, 51: tube portion
22, 42, 52: brim portion
23, 43, 53: joining portion
24, 44, 54, 64: mouth
212, 412, 512: arcuate sloping surface
612: mouth edge rim
G: cast

The invention claimed is:
1. An external-injury waterproof protector comprising:
a flexible pouch body composed of a waterproofing material and having an opening in either a single end or in both of opposing ends of the flexible pouch body; and
either a single radially extensible/contractible annular constriction component hermetically and adhesively attached to the opening on the one end of the flexible pouch body, or a pair of radially extensible/contractible annular constriction components hermetically and adhesively attached to both of the opposing ends of the flexible pouch body, the single annular constriction component including, or the pair of annular constriction components each including,
a joining portion where the annular constriction component attaches to the flexible pouch body,
a tube portion joined to the joining portion and the entirety of which is formed at a narrower diameter than that of the opening in the single end or the openings in both of the opposing ends of the flexible pouch body, and opening in a mouth-end of the annular constriction component, the tube portion adapted for covering a portion of any the four human limbs in a watertight state, and a brim portion formed projecting radially outward from a peripheral edge of the tube portion, the brim portion arcuately sloping gently in a flaring form furnishing the mouth-end of the annular constriction component with an arcuate sloping surface.

2. The external-injury waterproof protector set forth in claim 1, wherein the annular constriction component is composed of silicone rubber.

3. The external-injury waterproof protector set forth in claim 2, wherein the flexible pouch body is composed from polyvinyl chloride, polyurethane, or α olefins.

4. The external-injury waterproof protector set forth in claim 2, wherein the flexible pouch body and the annular constriction component are welded to each other by heat sealing.

5. The external-injury waterproof protector set forth in claim 2, wherein the flexible pouch body and the annular constriction component are bonded using a cement having a cyanoacrylate as its principal component.

6. The external-injury waterproof protector set forth in claim 1, wherein the flexible pouch body is composed from polyvinyl chloride, polyurethane, or α olefins.

7. The external-injury waterproof protector set forth in claim 6, wherein the flexible pouch body and the annular constriction component are welded to each other by heat sealing.

8. The external-injury waterproof protector set forth in claim 6, wherein the flexible pouch body and the annular constriction component are bonded using a cement having a cyanoacrylate as its principal component.

9. The external-injury waterproof protector set forth in claim 1, wherein the flexible pouch body and the annular constriction component are welded to each other by heat sealing.

10. The external-injury waterproof protector set forth in claim 3, wherein the flexible pouch body and the annular constriction component are welded to each other by heat sealing.

11. The external-injury waterproof protector set forth in claim 3, wherein the flexible pouch body and the annular constriction component are bonded using a cement having a cyanoacrylate as its principal component.

12. The external-injury waterproof protector set forth in claim 1, wherein the flexible pouch body and the annular constriction component are bonded using a cement having a cyanoacrylate as its principal component.

* * * * *